United States Patent
Bender et al.

(10) Patent No.: US 9,598,332 B2
(45) Date of Patent: Mar. 21, 2017

(54) PRODUCTION OF PARA-XYLENE

(71) Applicant: ExxonMobil Chemical Patents Inc., Baytown, TX (US)

(72) Inventors: Timothy P. Bender, Houston, TX (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 188 days.

(21) Appl. No.: 14/533,856

(22) Filed: Nov. 5, 2014

(65) Prior Publication Data
US 2015/0175507 A1   Jun. 25, 2015

Related U.S. Application Data

(60) Provisional application No. 61/918,903, filed on Dec. 20, 2013.

(51) Int. Cl.
| | |
|---|---|
| *C07C 7/13* | (2006.01) |
| *C07C 5/22* | (2006.01) |
| *C07C 5/23* | (2006.01) |
| *C07C 5/27* | (2006.01) |
| *C07C 2/86* | (2006.01) |
| *C07C 7/163* | (2006.01) |

(52) U.S. Cl.
CPC ............. *C07C 7/13* (2013.01); *C07C 2/864* (2013.01); *C07C 2/865* (2013.01); *C07C 5/2737* (2013.01); *C07C 7/163* (2013.01); *C07C 2529/08* (2013.01); *C07C 2529/18* (2013.01); *C07C 2529/40* (2013.01); *C07C 2529/70* (2013.01)

(58) Field of Classification Search
None
See application file for complete search history.

(56) References Cited

U.S. PATENT DOCUMENTS

| | | |
|---|---|---|
| 6,368,496 B1 | 4/2002 | Brown et al. |
| 6,423,879 B1 | 7/2002 | Brown et al. |
| 6,504,072 B1 | 1/2003 | Brown et al. |
| 2004/0087823 A1* | 5/2004 | McMinn ............... C07C 5/2737 585/481 |
| 2007/0112240 A1 | 5/2007 | Brown et al. |
| 2007/0249882 A1 | 10/2007 | Ou et al. |
| 2010/0152508 A1 | 6/2010 | Ou et al. |

(Continued)

*Primary Examiner* — In Suk Bullock
*Assistant Examiner* — Philip Louie

(57) ABSTRACT

In a process for producing para-xylene, a feed comprising a mixture of xylene isomers, olefinic unsaturated contaminants and oxygenate contaminants is supplied to a para-xylene recovery unit to recover para-xylene and produce a para-xylene depleted residual stream. The para-xylene depleted residual stream is then contacted with a xylene isomerization catalyst in a xylene isomerization zone under liquid phase conditions effective to isomerize xylenes and produce an isomerized product having a higher para-xylene content than the para-xylene depleted residual stream. The isomerized product is then recycled to the para-xylene recovery unit. At least one of the feed, the para-xylene depleted residual stream and the isomerized product is contacted with a solid acid catalyst in a treatment zone under conditions effective to reduce the level of olefinic unsaturated contaminants and oxygenate contaminants therein and produce a treated stream.

21 Claims, 2 Drawing Sheets

(56) References Cited

U.S. PATENT DOCUMENTS

2010/0261941 A1* 10/2010 Hagemeister .......... C07C 2/864
　　　　　　　　　　　　　　　　　　　　　　585/470
2011/0263918 A1　　10/2011　Ou et al.
2013/0324780 A1　　12/2013　Ou et al.

* cited by examiner

PRODUCTION OF PARA-XYLENE

CROSS REFERENCE TO RELATED APPLICATIONS

This application claims priority to and the benefit of U.S. Ser. No. 61/918,903, filed on Dec. 20, 2013, the disclosure of which is incorporated herein by reference in its entirety.

FIELD OF THE INVENTION

This invention relates to a process for the production of para-xylene.

BACKGROUND OF THE INVENTION

Para-xylene is an important aromatic hydrocarbon, for which the worldwide demand is steadily increasing. The demand for para-xylene has increased in proportion to the increase in demand for polyester fibers and film and typically grows at a rate of 5-7% per year.

Major sources of para-xylene are the aromatic streams derived from processes such as naphtha reforming and thermal cracking (pyrolysis). These complex streams are initially fractionated to separate a $C_8$-containing fraction, which is then fed to a para-xylene production loop where para-xylene is recovered, generally by adsorption or crystallization, and the resultant para-xylene depleted stream is subjected to catalytic conversion to isomerize the xylenes back towards equilibrium distribution. Xylene isomerization can be conducted under gas phase or liquid phase conditions, but increasingly liquid phase operation is preferred to reduce ring loss and by-product formation.

Aromatic streams derived from naphtha reforming and thermal cracking generally contain undesirable olefinic hydrocarbon contaminants, including mono-olefins, dienes, and styrenes, which can adversely affect the downstream para-xylene production process and so must be removed or reduced to very low levels. Undesirable hydrocarbon contaminants containing olefinic bonds are quantified by their Bromine Index (BI) and have typically been removed from aromatic streams, such as BTX streams, by contacting the streams with acid-treated clays. Other materials, e.g., zeolites, have also been used for this purpose. For example, U.S. Pat. No. 6,368,496 discloses a process in which a BTX stream derived from reformate is initially treated with a clay or hydro-treating catalyst to selectively remove dienes and then the resulting essentially diene-free effluent stream is contacted with a crystalline molecular sieve material, such as MCM-22, to selectively remove mono-olefins.

U.S. Pat. No. 7,744,750 discloses a process for reducing the Bromine Index of an aromatic hydrocarbon feedstock wherein the process comprises (a) pretreating the feedstock with a catalyst or absorbent to reduce oxygenates-oxygen in the feedstock to less than 5 wppm and then (b) contacting the pretreated feedstock with a catalyst comprising a molecular sieve having an MWW structure type, such as MCM-22. The effluent from step (b) may then be fed to a para-xylene production process. See also U.S. Patent Application Publication No. 2013/0324780.

Recently, there has been increasing interest in developing additional sources of para-xylene. For example, the benzene and/or toluene component of reformate can be used to produce additional para-xylene by reaction with methanol or dimethyl ether over a para-selective catalyst, such as severely steamed ZSM-5. An example of such a process is described in U.S. Pat. Nos. 6,423,879 and 6,504,072.

One problem associated with using the alkylation of benzene and/or toluene with methanol and/or dimethyl ether as a source of para-xylene is that the alkylation product inevitably contains a variety of oxygenate by-products as a result of side reactions of methanol with itself and the various aromatic species present. Such oxygenate by-products include water, alcohols, ethers, ketones, aldehydes, acid and phenolic impurities and, depending on their boiling point, are either returned to the alkylation reactor in recycle streams or leave the process through one or more product streams. In particular, the para-xylene-rich product stream tends to contain phenolic impurities, such as phenol, methyl phenols and dimethyl phenol, at levels from ten to several hundred ppmw. At such high levels, these phenolic impurities are unlikely to be processed in the para-xylene separation unit or the xylene isomerization unit and so may build up in the xylene production loop. Such a build-up not only occupies excess capacity in the paraxylene separation unit, thereby reducing its efficiency, but can also contaminate the paraxylene product and/or the para-xylene depleted residual stream which then can result in reduced performance of the xylene isomerization unit. Oxygenates may also potentially lead to equipment fouling.

There is therefore a need for an effective process for removing olefinic unsaturated hydrocarbon contaminants, such as styrenes, and oxygenate impurities, such as phenolic compounds, from xylene-containing streams, particularly those produced by the alkylation of benzene and/or toluene with methanol and/or dimethyl ether. Similar requirements apply to bio-derived aromatics feedstocks, since these typically contain trace levels of both oxygenate and olefinic impurities.

SUMMARY OF THE INVENTION

According to invention it has now been found that certain solid acid catalysts, particularly MWW structure type molecular sieves, are effective in removing oxygenates, such as phenolic compounds, as well as unsaturated hydrocarbons, such as styrene, from xylene-containing streams. As a result it is possible to close couple an MWW pretreatment catalyst with a liquid phase isomerization catalyst to provide a cost-effective method of producing para-xylene from the xylene-containing product streams from the alkylation of benzene and/or toluene with methanol and/or dimethyl ether while reducing or preventing the build-up of oxygenate contaminants in the para-xylene production loop. The present process is equally effective for processing other aromatics feedstocks containing olefinic and oxygenated impurities, such as bio-derived aromatics feedstocks and those produced from coal and/or syngas.

Accordingly, in one aspect, a process for producing para-xylene with a reduced amount of olefinic unsaturated and/or oxygenate contaminants is provided. A feed comprising a mixture of xylene isomers and having olefinic unsaturated contaminants and oxygenate contaminants therein is supplied to a para-xylene recovery unit to recover para-xylene from the feed and produce a para-xylene depleted residual stream. At least a part of the para-xylene depleted residual stream is then contacted with a xylene isomerization catalyst in a xylene isomerization zone under substantially liquid phase conditions effective to isomerize xylenes in the para-xylene depleted residual stream and produce an isomerized product having a higher para-xylene content than the para-xylene depleted residual stream, which is recycled to the para-xylene recovery unit. At least one stream selected from the feed, the para-xylene depleted residual stream and the isomerized product is contacted with a solid acid catalyst in a treatment zone under conditions effective to reduce the level of olefinic unsaturated contaminants and/or oxygenate contaminants therein and produce a treated stream.

The feed may be the product of reacting benzene and/or toluene with methanol in the presence of a molecular sieve catalyst under alkylation conditions to produce an alkylation effluent comprising xylenes, which may have a Bromine Index of 5 to 2,000 and at least 2 ppm by weight of oxygenate contaminants. Following treatment, the treated stream has a Bromine Index of less than that of the feed, such as less than 20, desirably less than 5, and less than 0.1 ppm by weight of oxygenate contaminants. In one embodiment, the solid acid catalyst comprises a clay and/or a molecular sieve, desirably a MWW structure type molecular sieve. In a preferred embodiment, the xylene isomerization zone and the treatment zone are connected in series, for example in the same reactor.

In a further aspect, the invention resides in a process for reducing the level of olefinic unsaturated contaminants and oxygenate contaminants in an aromatic hydrocarbon feed by contacting the feed in the presence of hydrogen with a catalyst comprising a MWW structure type molecular sieve under conditions effective to reduce the level of olefinic unsaturated contaminants and oxygenate contaminants in the feed and produce a treated feed.

DETAILED DESCRIPTION OF THE INVENTION

Figure 1:
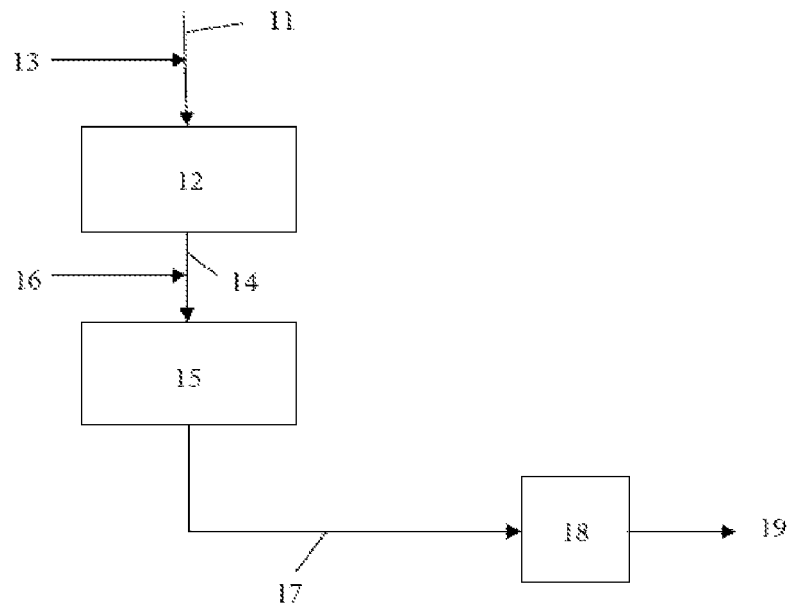
FIG. 1 is a simplified flow diagram of a liquid phase xylene isomerization process employing feed pretreatment according to a first example of the invention.

Described herein is a process for reducing the Bromine Index of an aromatic hydrocarbon feedstock also containing oxygenate impurities by contacting the feedstock, optionally in the presence of hydrogen, with a solid acid catalyst under conditions effective to reduce the level of olefinic unsaturated contaminants and oxygenate contaminants in the feedstock. The present treatment process is particularly intended for use with xylene-containing feedstocks since the resultant treated feedstock can then feed to a para-xylene production process employing a liquid phase isomerization catalyst without deleterious build-up of olefinic and oxygenate contaminants in the production loop. The stability of the feed treatment catalyst and/or the isomerization catalyst may be maintained by controlling the temperature of the relevant reaction, hydrogen addition or a combination thereof.

As used herein, Bromine Index is an indicator of the presence of olefinic bonds and is a measure of the number of milligrams of bromine consumed by 100 grams of a sample containing olefinic unsaturation under a given set of test condition as specified in ASTM D 2710-92.

Feedstock

Any aromatic hydrocarbon feedstock can be used in the present process including those obtained from reforming and cracking processes, as well as aromatic streams derived from biological sources. Suitable aromatic feedstocks have a Bromine Index of at least 5, such as from 5 to 2000, for example from 20 to 1000, as a result of olefinic contaminants, such as styrene, and also contain at least 2 ppmw, such as at least 5 ppmw, such as from 5 to 2000 ppmw, for example from 10 to 1000 ppmw of oxygenates, especially oxygenates co-boiling with xylenes, such as carbonyls, phenol and/or substituted phenols. Preferred feedstocks are $C_8$ aromatic hydrocarbon streams containing a mixture of xylene isomers.

In one embodiment, the aromatic hydrocarbon feedstock is the para-xylene rich $C_8$ aromatic hydrocarbon fraction resulting from reacting benzene and/or toluene with methanol and/or dimethyl ether in the presence of a catalyst comprising a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa). The porous crystalline material is preferably a medium-pore zeolite, particularly ZSM-5, which has been severely steamed at a temperature of at least 950° C. The porous crystalline material may be combined with at least one oxide modifier, such as an oxide of phosphorus, to control reduction of the micropore volume of the material during the steaming step. The methylation reaction may be conducted at a temperature from 500 to 700° C., a pressure from 100 to 7000 kPa, a weight hourly space velocity of from 0.5 to 1000 hr$^{-1}$, and a molar ratio of toluene to methanol (in the reactor charge) from 0.2 to 20. The process may be conducted in the presence of added hydrogen and/or added water such that the molar ratio of hydrogen and/or water to toluene+methanol in the feed is from 0.01 to 10. Under these conditions para-xylene may be produced at a selectivity of at least 90 wt % (based on total $C_8$ aromatic product) at a per-pass toluene conversion of at least about 15 wt % and a trimethylbenzene production level less than 1 wt %. Further details of this process can be found in U.S. Pat. Nos. 6,423,879 and 6,504,072, the entire contents of which are incorporated herein by reference. The product of the toluene methylation reaction will generally be fractionated to obtain the para-xylene rich $C_8$ aromatic hydrocarbon feedstock employed in the present process.

It is to be appreciated that other less para-selective or even non-selective methylation processes can also be used to generate the xylene-containing aromatic hydrocarbon feedstocks employed in the present process.

In addition, the present process can be used to treat other aromatic hydrocarbon streams containing olefinic and oxygenate contaminants. Non-limiting examples of such other aromatic hydrocarbon streams include those produced from methanol, such as by the well known methanol to gasoline and methanol to aromatics processes, and bio-derived aromatics feedstocks. For example, U.S. Published Patent Application No. 2013/0245316 discloses that cellulose and/or hemicellulose may be converted into 2,5-dimethylfuran (DMF), which in turn may be converted into para-xylene by cycloaddition of ethylene. In addition, U.S. Pat. No. 8,455,705 discloses a three stage process for producing aromatics from biomass, in which the biomass is first converted to water soluble oxygenated hydrocarbons, which are then reacted with hydrogen in the presence of a reforming catalyst to produce lower oxygenates which can then be converted to $C_{4+}$ hydrocarbons by a vapor phase process over an acid catalyst. Further, U.S. Pat. No. 8,277,643 discloses a process for producing BTX by catalytic pyrolysis of a solid hydrocarbonaceous material, such as lignocellulosic biomass.

Feedstock Treatment

In accordance with the present process, treatment of an aromatic hydrocarbon feedstock as described above comprises contacting the feedstock with a solid acid catalyst in a treatment zone under conditions effective to reduce the Bromine Index of the feedstock and reduce the level of oxygenate contaminants therein. Suitable solid acid catalysts include clays, molecular sieves and mixtures thereof. Catalysts containing molecular sieves are generally preferred.

Clay catalysts useful in the present process include acidic naturally-occurring clays as well as synthetic clay materials. Naturally-occurring clays include those of the montmorillonite and kaolin families. One preferred clay is F-24X clay produced by BASF Corporation. However, several other types of clay are available commercially and are suitable for use in the present process, including Filtrol 25 and Filtrol 62 produced by the BASF Corporation, Attapulgus clay and the Tonsil clay family produced by Sud Chemie. In some embodiments, the clays are pretreated with acid, such as HCl or $H_2SO_4$.

Molecular sieves useful in the present process include any of the naturally occurring or synthetic crystalline molecular sieves. Examples include large pore zeolites, intermediate pore size zeolites, and small pore zeolites. These zeolites and their isotypes are described in "Atlas of Zeolite Structure Types", Eds. Ch. Baerlocher, L. B. McCusker and D. H. Olson, Elsevier, Sixth Edition, 2007, the contents of which is hereby incorporated by reference. A large pore zeolite generally has a pore size of at least 7 Å, and includes LTL, VFI, MAZ, MEI, FAU, EMT, OFF, BEA, MTW, MWW, and MOR structure type zeolites (IUPAC Commission of Zeolite Nomenclature). Examples of large pore zeolites include mazzite, offretite, zeolite L, VPI-5, zeolite Y, zeolite X, omega, Beta, ZSM-3, ZSM-4, ZSM-12, ZSM-18, ZSM-20, SAPO-37, and MCM-22. An intermediate pore size zeolite generally has a pore size from 5Å to 7Å and includes, for example, MFI, MEL, MTW, EUO, MTT, MFS, AEL, AFO, HEU, FER, and TON structure type zeolites (IUPAC Commission of Zeolite Nomenclature). Examples of intermediate pore size zeolites include ZSM-5, ZSM-11, ZSM-22, ZSM-23, ZSM-34, ZSM-35, ZSM-385, ZSM-48, ZSM-50, ZSM-57, silicalite 1, and silicalite 2. A small pore size zeolite has a pore size from 3Å to 5Å and includes, for example, CHA, ERI, KFI, LEV, SOD, and LTA structure type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, hydroxysodalite, erionite, chabazite, zeolite T, gmelinite, ALPO-17, and clinoptilolite.

The molecular sieve employed in the present process is usually a large pore size zeolite or an intermediate pore size zeolite. Preferred molecular sieves include ZSM-12, mordenite, Zeolite Beta, USY and particularly molecular sieves having a MWW structure type, e.g., MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Patent No 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use in the present process. Mesoporous molecular sieves, such as such as M41 S (U.S. Pat. No. 5,102,643) and MCM-41 (U.S. Pat. No. 5,098,684) may also be used.

One measure of the acid activity of a molecular sieve is its Alpha Value, which is an approximate indication of the catalyst acid activity and gives the relative rate constant (rate of normal hexane conversion per volume of catalyst per unit time). It is based on the activity of the highly active silica-alumina cracking catalyst taken as an Alpha of 1 (Rate Constant=0.16 sec$^{-1}$). The Alpha Value is described in U.S. Pat. No. 3,354,078, in the Journal of Catalysis, Vol. 4, p. 527 (1965); Vol. 6, p. 278, and Vol. 61, p. 395 (1980), each of which is herein incorporated by reference as to that description. The experimental conditions of the test used include a constant temperature of 538° C., and a variable flow rate as described in the Journal of Catalysis, Vol. 61, p. 395 (1980). In one embodiment, the molecular sieve employed in the present process has an Alpha Value at least 1, preferably at least 10, more preferably at least 50, even more preferably at least 100, for example from 100 to 1000.

The crystalline molecular sieve may be used in unbound form or it may be composited with a matrix material, including synthetic and naturally occurring substances, such as clay, silica, alumina, zirconia, titania, silica-alumina, and other metal oxides. Other porous matrix materials include silica-magnesia, silica-zirconia, silica-thoria, silica-beryllia, silica-titania, as well as ternary compositions such as silica-alumina-thoria, silica-alumina-zirconia, silica-alumina-magnesia, and silica-alumina-zirconia. The catalyst can be used in the form of an extrudate, lobed form (e.g., trilobe), or powder.

Regenerated molecular sieve catalysts such as those described in U.S. Pat. No. 8,329,971, the entire contents of which are incorporated herein by reference, can also be used in the present feed treatment process.

Contacting of the aromatic hydrocarbon feedstock with the solid acid catalyst described above may be conducted over a wide range of conditions, although generally the pressure and temperature are controlled so as to maintain the hydrocarbon substantially in the liquid phase. Embodiments include a temperature from 150° C. to 370° C., for example 230° C. to 280° C., a pressure from 300 kPa absolute to 5000 kPa absolute, and a weight hourly space velocity from 0.3 hr$^{-1}$ absolute to 50 hr$^{-1}$. The contacting may be conducted in the presence or absence of hydrogen. It is, however, found that the presence of hydrogen improves catalyst stability. Suitable hydrogen levels include at least 3 wt-ppm of the aromatic hydrocarbon stream, such as from 7 to 15 wt-ppm of the aromatic hydrocarbon stream.

The treated aromatic hydrocarbon resulting from the contacting with the solid acid catalyst as described above has a lower Bromine Index and a lower oxygenate content than the untreated feedstock. In one embodiment, the treated aromatic hydrocarbon has a Bromine Index less than 50%, preferably less than 20%, more preferably less than 10%, of the Bromine Index of the untreated hydrocarbon feedstock and an oxygenate content less than 70%, for example less than 50%, preferably less than 20%, more preferably less than 10%, of the oxygenate content of the untreated hydrocarbon feedstock. For example, the treated aromatic hydrocarbon may have a Bromine Index less than 200, for example less than 20, such as less than 5 and an oxygenate content, especially oxygenates co-boiling with xylenes, less than 50 ppm by weight, such as less than 5 ppm by weight, for example less than 1 ppm by weight. Achieving the lower levels of Bromine Index and oxygenate contaminants may require distillation of the treated aromatic hydrocarbon to remove heavy-by-products produced during the treatment step.

Production of Para-Xylene

In one preferred embodiment, the aromatic hydrocarbon feedstock employed herein is a mixture of xylene isomers used in a process for producing para-xylene that includes liquid-phase xylene isomerization. In such a process, the aromatic hydrocarbon feedstock is initially supplied to a para-xylene recovery unit, where para-xylene is recovered from the feedstock by any known method, normally crystallization and/or adsorption, to leave a para-xylene depleted residual stream). The para-xylene depleted residual stream is then fed to a xylene isomerization zone where the para-xylene depleted residual stream is contacted with a xylene isomerization catalyst under substantially liquid phase conditions effective to isomerize xylenes in the para-xylene depleted residual stream and produce an isomerized product having a higher para-xylene content than the para-xylene depleted residual stream. A suitable liquid phase xylene isomerization process is described in U.S. Published Patent Application No. 2011/0263918, the entire contents of which are incorporated herein by reference. This process utilizes a catalyst comprising HZSM-5 or MCM-49 and conditions including a temperature of less than 295° C. and a pressure sufficient to maintain the xylenes in the liquid phase. In embodiments, the process can be operated in a continuous mode with wppm levels of dissolved $H_2$, up to saturation levels of dissolved $H_2$, in the feed so as to improve catalyst stability.

At least part of the isomerized product from liquid phase xylene isomerization process is then recycled to the para-xylene recovery unit such that the para-xylene recovery unit and the xylene isomerization zone define a para-xylene production loop. In accordance with one aspect of the present invention, one or more process streams associated with this para-xylene production loop are treated with a solid acid catalyst in the manner described above. Exemplary process streams include the mixture of xylene isomers supplied to the para-xylene recovery unit, the para-xylene depleted residual stream and the isomerized product stream.

In one preferred embodiment, the treatment zone and the xylene isomerization zone are connected in series, with either solid acid treatment catalyst or the xylene isomerization catalyst in the upstream position. In the former case, the solid acid treatment is conducted on the para-xylene depleted residual stream, whereas in the latter case the solid acid treatment is conducted on the isomerized product.

Conveniently, the treatment zone and the xylene isomerization zone are connected in series such that intermediate processing such as fractionation is avoided. For example, the solid acid treatment catalyst and the xylene isomerization catalyst could be housed in a single reaction zone, which is some embodiments could include a reactive distillation unit. Alternatively, the solid acid treatment catalyst and the xylene isomerization catalyst could be housed in separate reaction zones connected in series without intermediate separation of the reaction effluent between reaction zones. In this way, a single fractionation step can be used to separate any light or heavy by-products from both the treatment step and the xylene isomerization step. Other process units, such as a surge drum or a pump, can of course be interposed between the treatment zone and the xylene isomerization zone.

The invention will now be more particularly described with reference to the accompanying drawings, which show six, non-limiting examples of the use of the present pretreatment process in the liquid phase isomerization of a mixed xylenes-containing hydrocarbon stream.

Referring initially FIG. 1, in a first example, a mixed xylenes-containing hydrocarbon feed containing olefinic and oxygenate contaminants is supplied by line 11 to a feed treatment unit 12, which also optionally receives a supply of hydrogen through line 13. In some embodiments, the line 11 may also supply to the unit 12 one or more further xylene-containing aromatic hydrocarbon streams substantially free of olefinic and/or oxygenate contaminants, such as those derived from reformate or steam cracked naphtha, as well as $C_8+$ fractions from transalkylation and disproportionation processes.

The treatment unit 12 contains a solid acid catalyst comprising clay and/or molecular sieve and is operated under conditions effective to reduce the level of olefinic and oxygenate contaminants in the feed and produce a treated stream, which exits the unit 12 through line 14. The treated stream is fed by line 14 to a liquid phase xylene isomerization unit 15 which is connected in series with the unit 12 and which optionally receives a supply of hydrogen through line 16. In embodiments, hydrogen can be supplied to one, both or neither of the units 12 and 15.

The xylene isomerization unit 15 contains a xylene isomerization catalyst which is operated under substantially liquid phase conditions effective to isomerize xylenes in the treated stream and produce an isomerized product having a higher para-xylene content than the treated stream. The treated product exits the unit 15 via line 17 and is then fed to a fractionation system 18 to remove higher and/or lower boiling components and leave a para-xylene enriched C8 fraction which is fed by line 19 to a para-xylene recovery unit (not shown).

Figure 2:
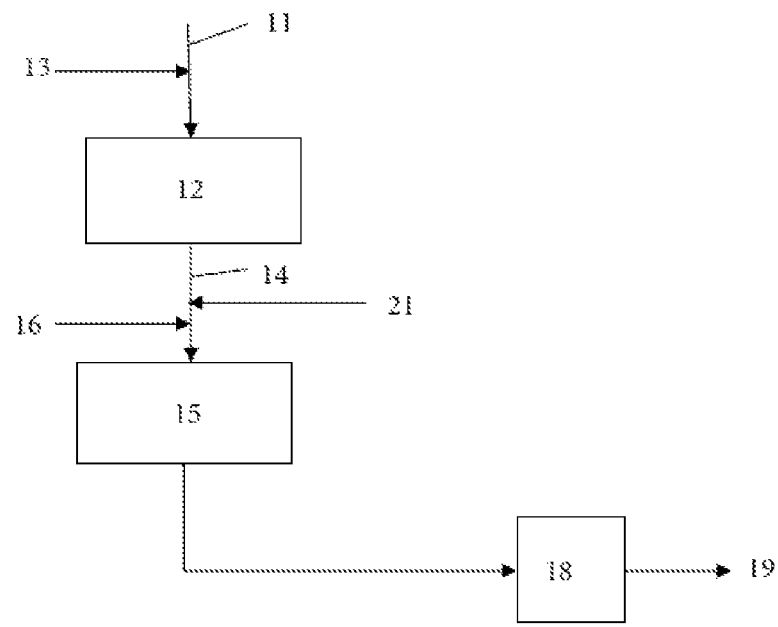
FIG. 2 is a simplified flow diagram of a modification of the process shown in FIG. 1.

A modification of the process of the first example is shown in FIG. 2, where like components are indicated by like reference numerals. In this modification, one or more further xylene-containing aromatic hydrocarbon streams substantially free of olefinic and/or oxygenate contaminants is supplied by line 21 to the xylene isomerization unit 15 either instead of or in addition to any similarly uncontaminated aromatic hydrocarbon streams included in the feed supplied by line 11.

Figure 3:
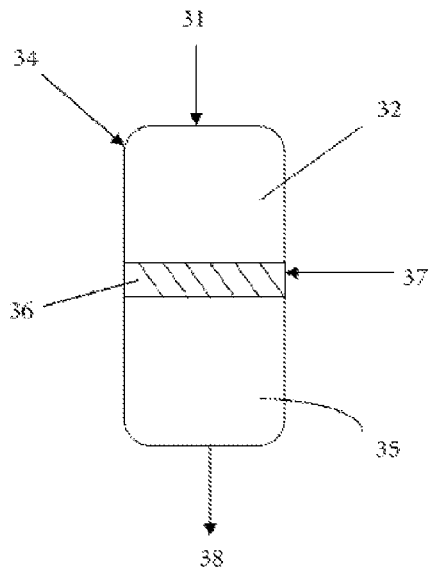
FIGS. 3-6 are simplified flow diagrams of isomerization processes according to embodiments of the invention.

A second example is shown in FIG. 3, in which a mixed xylenes-containing hydrocarbon feed containing olefinic and oxygenate contaminants, optionally together with one or more further xylene-containing aromatic hydrocarbon streams substantially free of olefinic and/or oxygenate contaminants, is supplied by line 31 to a feed treatment zone 32. The feed treatment zone 32 is contained in the same reactor 34 as a liquid phase xylene isomerization zone 35, but is separated therefrom by reactor internals 36. An optional supply of hydrogen is fed by line 37 through the reactor internals 36 to the liquid phase xylene isomerization zone 35. The treatment and xylene isomerization steps of the process of the second example operate in the same way as the process of the first example to produce an isomerized product which exits the reactor 34 through line 38 and can be fed to a downstream fractionation system (not shown) and then a para-xylene recovery unit (not shown).

Figure 4:
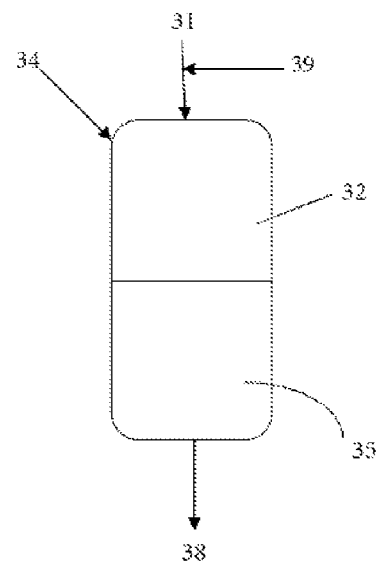

A modification of the process of the second example is shown in FIG. 4, where like components are indicated by like reference numerals. In this modification, the optional supply of hydrogen is routed to the feed treatment zone 32 via line 39.

Figure 5:
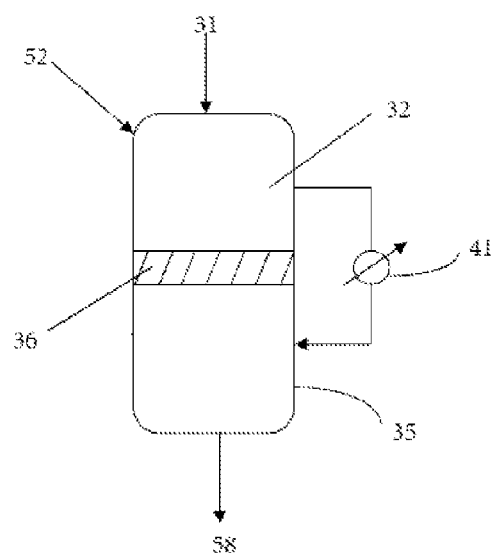

A further modification of the process of the second example is shown in FIG. 5, again with like components being indicated by like reference numerals. In this further modification, a side stream from the feed treatment zone 32 is fed to liquid phase xylene isomerization zone 35 by way of a heat exchanger 41 which allows feed treatment zone 32 and the liquid phase xylene isomerization zone 35 to be operated at different temperatures.

Figure 6:
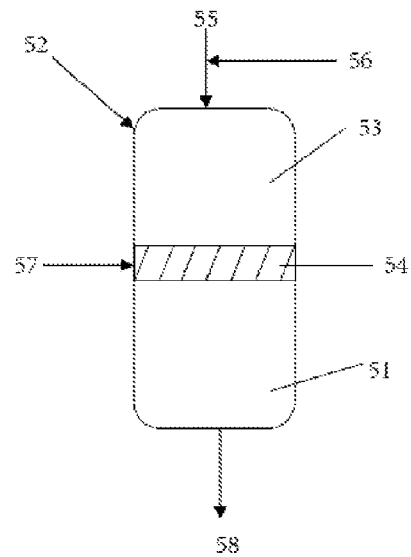

A third example is shown in FIG. 6, in which a feed treatment zone 51 is again contained in the same reactor 52 as a liquid phase xylene isomerization zone 53, but is separated therefrom by reactor internals 54. However, in this third example, a first xylene-containing aromatic hydrocarbon stream, which is substantially free of olefinic and/or oxygenate contaminants, is supplied by line 55 to the liquid phase xylene isomerization zone 53 optionally together with hydrogen supplied through line 56. The first stream contacts a xylene isomerization catalyst in the xylene isomerization zone 53 under substantially liquid phase conditions effective to isomerize xylenes in the first stream and produce an isomerized product having a higher para-xylene content than the first stream. The isomerized product flows through the reactor internals 54 to the feed treatment zone 51 which also receives a second xylene-containing aromatic hydrocarbon stream containing both olefinic and oxygenate contaminants supplied via line 57. The resultant combined stream contacts a solid acid catalyst comprising clay and/or molecular sieve in the feed treatment zone 51 under conditions effective to reduce the level of olefinic and oxygenate contaminants in the combined stream and produce a treated stream, which exits the reactor 52 through line 58. The treated stream is then fed by line 58 to a downstream fractionation system (not shown) and then apara-xylene recovery unit (not shown).

The invention claimed is:

1. A process for producing para-xylene, the process comprising:
   (a) supplying a feed comprising a mixture of xylene isomers to a para-xylene recovery unit to recover para-xylene from the feed and produce a para-xylene depleted residual stream, wherein the feed has a Bromine Index from 5 to 2000 and comprises from 5 to 2000 ppm by weight of oxygenate contaminants;
   (b) contacting at least part of the para-xylene depleted residual stream with a xylene isomerization catalyst in a xylene isomerization zone under substantially liquid phase conditions effective to isomerize xylenes in the para-xylene depleted residual stream and produce an isomerized product having a higher para-xylene content than the para-xylene depleted residual stream;
   (c) recycling at least part of the isomerized product to the para-xylene recovery unit; and
   (d) contacting at least one stream selected from the feed, the para-xylene depleted residual stream and the isomerized product with a solid acid catalyst in a treatment zone in the presence of 3-15 wt-ppm hydrogen and under conditions to reduce a level of olefinic unsaturated contaminants and oxygenate contaminants therein and produce a treated stream.

2. The process of claim 1, wherein the treated stream has a Bromine Index less than that of the feed and comprises a Bromine Index of less than 20.

3. The process of claim 1, wherein the olefinic unsaturated contaminants comprise styrene.

4. The process of claim 1, wherein the treated stream has a lower oxygenate content than the feed and comprises less than 50 ppm by weight of oxygenate contaminants.

5. The process of claim 1, wherein the oxygenate contaminants comprise phenol and/or substituted phenols.

6. The process of claim 1, wherein the solid acid catalyst comprises a clay, a molecular sieve or a mixture thereof.

7. The process of claim 1, wherein the solid acid catalyst comprises a molecular sieve selected from the group consisting of ZSM-12, mordenite, Zeolite Beta, USY, a MWW structure type molecular sieve, and mixtures thereof.

8. The process of claim 1, wherein the solid acid catalyst comprises a MWW structure type molecular sieve.

9. The process of claim 1, wherein the xylene isomerization zone and the treatment zone are connected in series.

10. The process of claim 1, wherein the contacting steps (b) and (d) are conducted in a single reaction zone.

11. The process of claim 1, wherein the contacting steps (b) and (d) are conducted in a separate reaction zones connected in series without intermediate separation.

12. The process of claim 1, wherein the contacting step (d) is conducted on the para-xylene depleted residual stream.

13. The process of claim 1, wherein the contacting step (d) is conducted on the isomerized product.

14. The process of claim 1, wherein the conditions in contacting step (d) include a temperature from 150° C. to 370° C.

15. The process of claim 1 and further comprising:
   (e) contacting benzene and/or toluene with methanol and/or dimethyl ether in the presence of a molecular sieve catalyst under alkylation conditions effective to react at least part of the methanol and/or dimethyl ether with at least part of the benzene and/or toluene to produce an alkylation effluent comprising xylenes; and
   (f) supplying at least part of the alkylation effluent as at least part of the feed in step (a).

16. The process of claim 15, wherein the catalyst employed in step (e) has a Diffusion Parameter for 2,2-dimethylbutane of about 0.1-15 sec$^{-1}$ when measured at a temperature of 120° C. and a 2,2-dimethylbutane pressure of 60 torr (8 kPa).

17. A process for reducing the level of contaminants in an aromatic hydrocarbon feed, wherein the feed has a Bromine Index from 5 to 2000 and comprises from 5 to 2000 ppm by weight of oxygenate contaminants, comprising contacting the feed in the presence of 3-15 wt-ppm hydrogen with a solid acid catalyst under conditions effective to reduce a level of olefinic unsaturated contaminants and oxygenate contaminants in the feed and produce a treated feed.

18. The process of claim 17, wherein the treated feed has a Bromine Index of less than 5 and comprises less than 5 ppm by weight of oxygenate contaminants.

19. The process of claim 17, wherein the solid acid catalyst comprises a molecular sieve selected from the group consisting of ZSM-12, mordenite, Zeolite Beta, USY, a MWW structure type molecular sieve and mixtures thereof.

20. The process of claim 17, wherein the conditions in the contacting step include a temperature from 150° C. to 370° C.

21. The process of claim 17, wherein the feed comprises $C_8$ aromatic hydrocarbons and the process further comprises supplying the treated feed to a para-xylene production loop comprising a para-xylene recovery unit and a liquid phase xylene isomerization unit.

* * * * *